United States Patent [19]

Jones et al.

[11] Patent Number: 4,940,797
[45] Date of Patent: Jul. 10, 1990

[54] PROCESS FOR SYNTHESIS OF FK-506 C10–C18 INTERMEDIATES

[75] Inventors: Todd K. Jones, Edison; Sander G. Mills, Woodbridge; Richard Desmond, Metuchen, all of N.J.

[73] Assignee: Merck & Co., Inc., Rahway, N.J.

[21] Appl. No.: 327,848

[22] Filed: Mar. 23, 1989

[51] Int. Cl.$^5$ .................... C07D 263/04; C07C 41/00; C07C 41/12; C07C 43/00
[52] U.S. Cl. .................................. 548/110; 568/679; 568/680; 568/682
[58] Field of Search ................ 568/659; 548/110, 215; 546/304

[56] References Cited

U.S. PATENT DOCUMENTS 4,487,963 12/1984 Bock et al. ........................ 548/215

OTHER PUBLICATIONS

S. Nahm et al., *Tetrahedron Lett.*, 22, No. 39, pp. 3815–3818, 1981.
"Introduction to Organic Chemistry", Streitwieser and Heathcock 1981, 2nd Ed.
"Organic Chemistry", Morrison and Boyd, 1983, 4th Ed.
Evans et al., "Direct Reduction of β-Hydroxy Ketones . . . ", J. Am. Chem. Soc. 110 3560–3578 (1988).

*Primary Examiner*—Anton H. Sutto
*Assistant Examiner*—Celia Chang
*Attorney, Agent, or Firm*—Robert J. North; Melvin Winokur; Charles M. Caruso

[57] ABSTRACT

A process is described for the improved synthesis of the optically pure $C_{10}$–$C_{18}$ fragment of the macrolide structure of the immunosuppressant FK-506. This compound is also useful as an intermediate for preparing FK-506 derivatives.

5 Claims, No Drawings

PROCESS FOR SYNTHESIS OF FK-506 C10–C18 INTERMEDIATES

BACKGROUND OF THE INVENTION

1. Field of the Invention

This invention relates to an improved process for producing the optically pure $C_{10}$–$C_{18}$ fragment of FK-506 useful as an intermediate in synthesizing the FK-506 immunosuppressant and derivatives thereof.

2. Brief Disclosures in the Art

The novel 23-membered tricyclo-macrolide FK-506 very recently isolated and characterized by Tanaka, Kuroda, and co-workers, see JACS, 109, pp. 5031, 1987, and EPO Publication No. 0184162, has been shown to possess exceptional immunosuppressive activity. The potential usefulness of such an agent in bone marrow and organ transplantations coupled with its unique structural features has prompted many in the field to initiate an effort towards the total synthesis of FK-506.

A highly diastereoselective synthesis of a protected C.10–C.18 subunit, in its correct absolute configuration, has already been achieved as reported by D. Askin, R. P. Volante, R. A. Reamer, K. M. Ryan and I. Shinkai in *Tetrahedron Letters*, 1988, 29, pp. 277–280. See also: (a) Villalobos, A.; Danishefsky, S. J., *J. Org. Chem.*, 1989, 54, pp. 15–16; (b) Schreiber, S. L.; Sammakia, T.; Uehling, D. E., *J. Org. Chem.*, 1989, 54, pp. 16–17.

However, this process, published by D. Askin et al., *Tetrahedron Letters*, 1988, pages 277 and 4245, requires 17 consecutive chemical steps to produce the key intermediate IX. Further, the method requires 3 isomer separations, which are both technically demanding and expensive. In addition, the method requires the use of an expensive reagent (R-pyrrolidinemethanol) in a 5-fold excess at an early stage of the process, also significantly increasing the overall expense.

What is constantly being searched for in the art are newer, more economical methods to produce FK-506 and its derivatives via an inexpensive and convenient total synthesis scheme.

SUMMARY OF THE INVENTION

We have discovered a new, more economical method for providing the optically pure $C_{10}$–$C_{18}$ FK-506 fragment which only requires 10 consecutive steps (14 overall) and requires only one isomer separation. The simplified processing for this general sequence is illustrated in following Flow Sheet A.

As seen, the method involves the preparation of the important precursor, 9, to the immunoregulant FR900506 (FK-506; L-679,934) (see Flow Sheet B). This compound with different protecting groups at $C_{14}$ and $C_{18}$ has been used as an intermediate in the total synthesis of FK-506 (see T. Jones et al, *J. Am. Chem. Soc.*, 1989, 111, 1157). The availability of compound 9 by this procedure will enable the synthesis of medicinally active analogs of FK-506.

By this invention there is provided a process comprising the steps of:

(a) Contacting III with an oxidizing agent in an inert solvent and of a temperature in the range from 0° to 50° C. for a

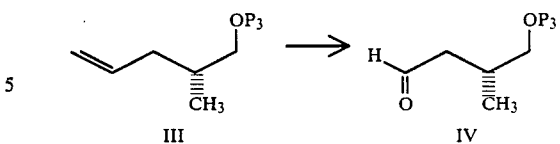

sufficient time to form the oxidation Product IV, where P is a hydroxy protecting group;

(b) Contacting IV with a solution of a chiral N-acyloxazolidinone XIV, where Y is protected oxymethyl, which is stable under the reaction conditions, and trialkylamine, and a dialkylboron fluoroalkylsulfonate under an inert atmosphere in an inert solvent and at a temperature in the range of −100° to 25° C. for a sufficient time to form the aldol addition product V, wherein $R_1$ and $R_2$ are independently chosen from H, $C_1$–$C_4$ linear or branched alkyl, benzyl, phenyl, which may be substituted with halo or $C_1$–$C_4$ alkoxy with the proviso that $R_2$ is not H;

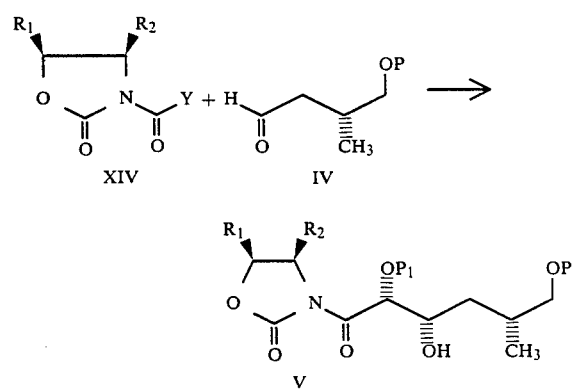

and where $P_1$ is a hydroxy protecting group which may be the same or different than P;

(c) Contacting V with a solution of a trialkylaluminum and N,O-dimethylhydroxylamine hydrochloride in an inert solvent and at a temperature in the range of −30° to 20° C. for a sufficient time to form the amide VI;

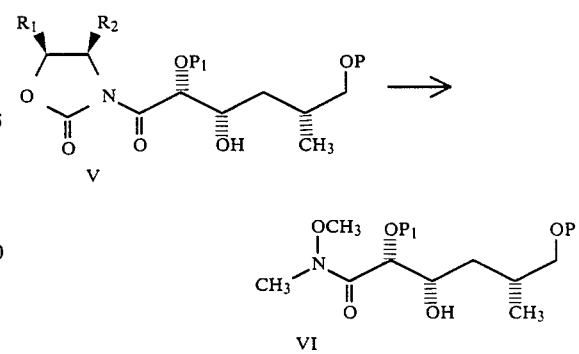

(d) Contacting VI with XIII in the presence of lithium in an inert solvent therefor at a temperature in the range of −100° to 25° C., followed

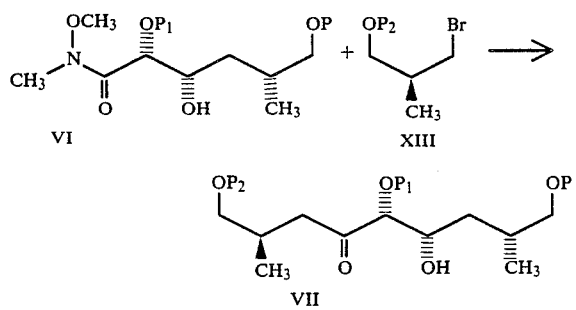

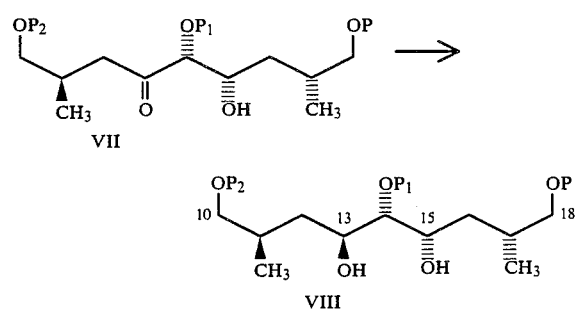

by contacting the resulting mixture with aqueous ammonium halide at a temperature in the range of −20° to 25° C. for a sufficient time to form the condensation product VII where $P_2$ is a hydroxy protecting group, which may be the same as $P_1$ but is different from P;

(e) Contacting VII with tetraalkylammonium triacetoxy borohydride and a weak organic acid in an inert solvent and at a temperature of about −40° to 25° C., for a sufficient time to form the reduction product VIII;

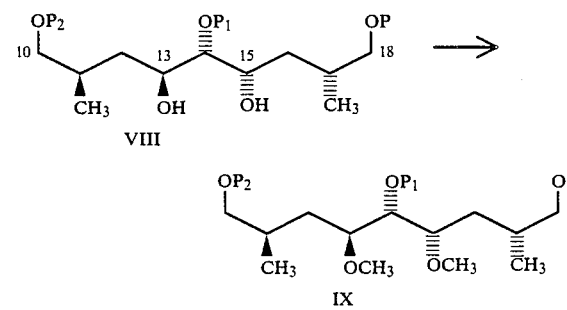

(f) Contacting VIII with an alkali metal hydride and a methylating agent under anhydrous conditions in an inert atmosphere in an inert solvent and at a temperature in the range of 0° to 50° C. for a sufficient time to form the methylated product IX;

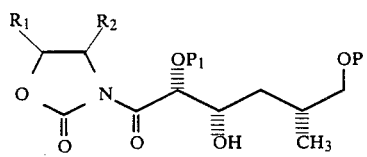

Further provided is a compound of the formula:

V where P and $P_1$ are independently hydroxy protecting groups, which may be the same or different, and $R_1$ and $R_2$ are independently selected from H, $C_1$–$C_4$ linear or branched alkyl, benzyl, phenyl, which may be substituted with halo or $C_1$–$C_4$ alkoxy, with the proviso that $R_2$ is not H.

Also provided is a compound of the structure:

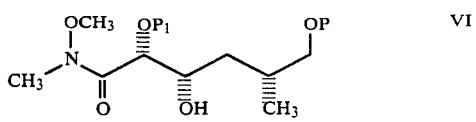

where P and $P_1$ are independently hydroxy protecting groups, which may be the same of different.

Furthermore, there is provided a compound of the structure:

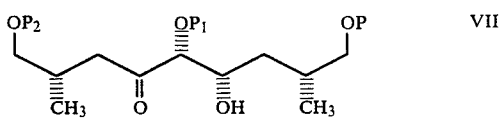

where P, $P_1$ and $P_2$ are independently hydroxy protecting groups, which may be the same or different, with the proviso that $P_2$ is different from P.

In addition, there is provided a compound of the structure:

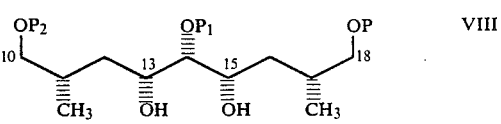

where P, $P_1$ and $P_2$ are independently hydroxy protecting groups, which may be the same or different, with the proviso that $P_2$ is different from P.

Also contemplated and included within the scope of the instant invention are the compounds specifically described above and herein which may have one, two or three unprotected hydroxy groups.

BRIEF DESCRIPTION OF THE INVENTION AND THE PREFERRED EMBODIMENTS

The invention can be readily understood by referring to the general synthesis scheme in Flow Sheet A.

The starting material III is known in the art and can be produced from compounds I and II by the methods described in the two references by Evans et al. hereinbelow, hereby incorporated by reference. The chiral substituent R is chosen from $C_1$–$C_4$ linear or branched alkyl, benzyl, phenyl, which may be substituted with halo or $C_1$–$C_4$ alkoxy. Preferred is benzyl. The hydroxy protecting groups described herein are conventional, as illustrated by P, and the class of hydroxy-protecting groups includes trisubstituted silyl, benzyl and substituted benzyl, and aroyl and alkanoyl. Preferred P for III is benzyl.

Hydroxy protecting groups, their structure, formation, removal and utility, are described in "Protective Groups in Organic Synthesis" by Theodora W. Greene, published by John Wiley, 1981, New York, Chapter 2, pages 10–87, titled "Protection for the Hydroxyl Group, Including 1,2- and 1,3-Diols".

Representative trisubstituted silyl groups, removable by acidic or fluoride hydrolysis are: trimethylsilyl, triethylsilyl, isopropyldimethylsilyl, t-butyldimethylsilyl (T-BuSi), (triphenylmethyl)dimethylsilyl, t-butyldiphenylsilyl, methyldiisopropylsilyl, methyldi-t-butylsilyl, tribenzylsilyl, tri-p-xylylsilyl, triisopropylsilyl, triphenylsilyl, and the like, preferably t-butyldimethylsilyl.
Flow Sheet A
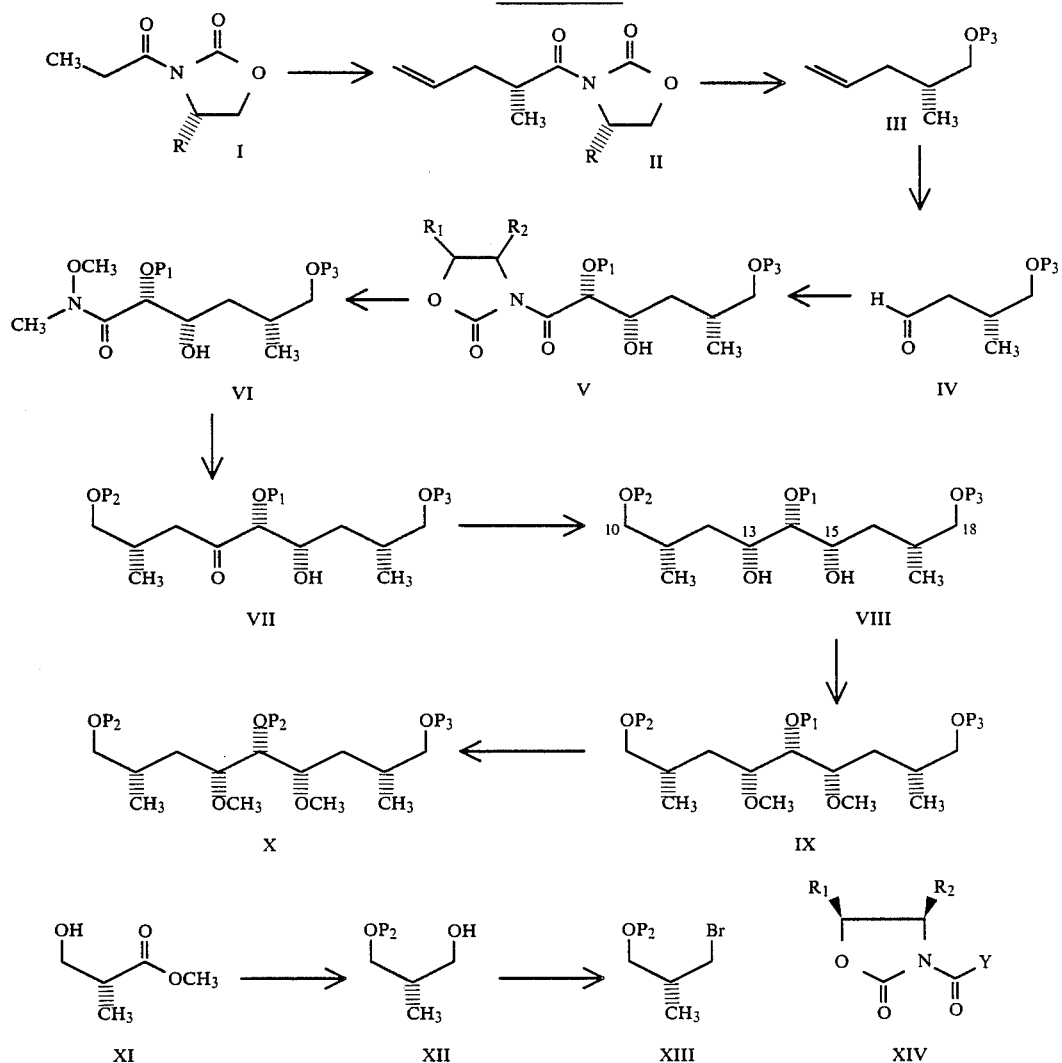
Flow Sheet B
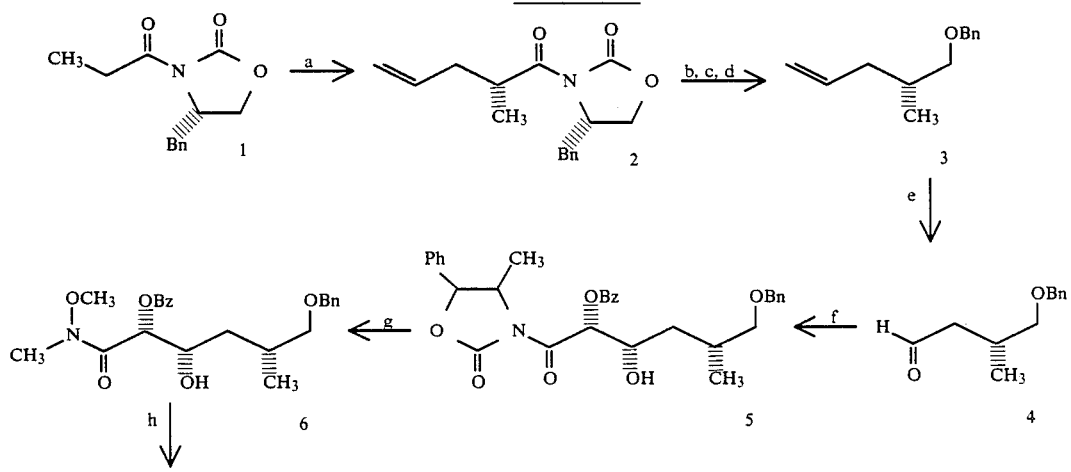

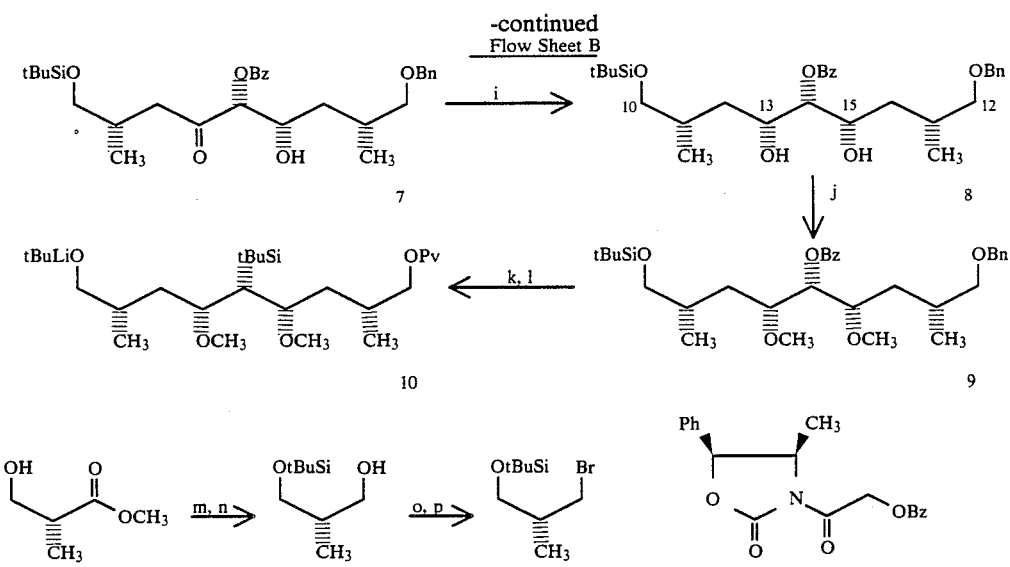

a NaHMDS, THF, −78° C. allyl iodide, −78° C.;
b LiOH, 30% H₂O₂, THF, H₂O, 0° C.;
c LAH, Et₂O, 0° C.;
d NaH, BnBr, DMF, 0–25° C.;
e OsO₄, KIO₄, acetone, water, 25° C.;
f 14, Bu₂BOTf, Et₃N, CH₂Cl₂, −50° C.; 4, −50° C.;
g Al(CH₃)₃, CH₃ONHCH₃·HCl, THF, 0–25° C.; 5, −10° C.;
h 6, THF, −78° C.; NH₄Cl/H₂O, 0° C.;
i (CH₃)₄NBH(OAc)₃, CH₃CN, HOAc, −20° C.;
j NaH, THF, CH₃I;
k H₂ Pd(OH)₂/C, EtOAc, 20° C.;
l i. PvCl, pyridine, 0° C.; ii. tBuSiOTf 2,6-lutidine, CH₂Cl₂, 0° C.;
m tBuSiCl, imidazole, DMF, 25° C.;
n Dibal, THF, −70–0° C.;
o CH₃SO₂Cl, Et₃N, CH₂Cl₂, −10° C.;
p Bu₄NBr, acetone, reflux Representative benzyl groups removed by catalytic hydrogenation or dissolving metal conditions, e.g. Li/NH₃ include: benzyl (Bn), 3,4-dimethoxybenzyl, p-methoxybenzyl (Bz), 6-nitrobenzyl, p-nitrobenzyl, p-bromobenzyl, p-chlorobenzyl, p-cyanobenzyl, and the like, preferably benzyl and p-methoxybenzyl.

Representative $C_1$–$C_{10}$ alkanoyl protecting groups removable by basiC hydrolysis or hydride reduction are: pivaloyl, isobutyroyl, adamantoyl, benzoyl, and the like, preferably pivaloyl.

The first step of the invention, referring to Flow Sheet A, is the synthesis of the butanal IV, accomplished by oxidation of alkene III.

Suitable oxidizing agents include osmium tetraoxide and potassium periodate, ozone, ruthenium tetraoxide, potassium permanganate, and the like. Preferred is the combination osmium tetraoxide/potassium periodate.

The oxidation is carried out in an inert solvent which is not oxidized by the reagent including $C_3$–$C_5$ ketones, which may be aqueous, e.g. acetone/H₂O, methylethyl ketone, and $C_2$–$C_4$ alcohols, e.g. ethanol, and the like. Preferred for the osmium tetraoxide/potassium periodate combination is ethanol/H₂O and acetone/H₂O.

The temperature of the oxidation is carried out in the range of 0° to 50° C., and preferably 25° to 30° C.

The molar ratio of the combination of osmium tetraoxide:potassium periodate:III is generally in the range of 0.01:2:1, where the osmium tetraoxide is used in catalytic amounts.

In general, times of 1 to 4 hours are required to achieve 80 to 90% yields.

As a specific example, referring to Flow Sheet B, the olefin ether 3 in acetone/water solvent is treated with aqueous osmium tetraoxide followed by potassium periodate at room temperature for six hours under a nitrogen atmosphere. Conventional workup yields the aldehyde 4 in 81% yield.

Conversion of IV to the aldol adduct V is illustrated in Flow Sheet A. $R_1$ and $R_2$ are independently selected from H, $C_1$–$C_4$ linear or branched alkyl, benzyl or phenyl, which may be substituted with halo, e.g. chloro, or $C_1$–$C_4$ alkoxy, e.g. methoxy, with the proviso that $R_2$ is not H. $P_1$ is selected from the same class conventional hydroxy protecting groups as described above for P, and is preferably p-methoxybenzyl (PMB).

IV is treated with a solution of an organic nitrogen base, dialkylboron fluoroalkylsulfonate and a chiral N-acyloxazolidinone XIV, where Y is a protected oxymethyl group, stable under the reaction conditions, including aralkyloxymethyl, e.g. benzyloxymethyl, p-methoxybenzyloxymethyl, and 2',2',2'-tri-chloroethoxymethyl to form the addition product V.

Suitable chiral N-acyloxazolidinone reagents, are commercially available, or made by procedures of Evans et al. J. Am. Chem. Soc. 103 2127-9 (1981) hereinbelow.

Representative examples of chiral N-acyloxazolidinones, which can be used in the process are: [4R,5R]-4-methyl-3-(1-oxo-2-(4'-methoxyphenylmethoxy)ethyl)-5-phenyl-2-oxazolidinone, [4R,5R]-4-methyl-3-(1-oxo-2-(2',2',2'-trichloroethoxy)ethyl)-5-phenyl-2-oxazolidinone (14), [4R,5R]-4-methyl-3-(1-oxo-2-(benzyloxy)ethyl-5-phenyl-2-oxazolidinone, including these compounds where the [4R] substituent is as defined above for $R_2$, e.g. methyl, ethyl, isopropyl, phenyl, benzyl, and the [5R] substituent is as defined above for $R_1$, e.g. H, methyl, ethyl, isopropyl, phenyl or benzyl, and the like. Preferred is the oxazolidinone 14, made by the procedure of Evans et al., *J. Am. Chem. Soc.* 103 2127-9 (1981) starting with norephedrine.

The organic nitrogen base functions as a hydrogen acceptor and can be a tertiary amine including trimethylamine, triethylamine, tri-n-butylamine, diisopropylethylamine, lutidine, and the like, preferably triethylamine.

The dialkylboron fluorosulfonate is used to form the enolate of XIV and is generally a $C_1$-$C_{10}$ linear or branched alkyl boron radical, e.g. diethyl, dipropyl, di-n-butyl boron radical, and the like, which may contain inert substituents, e.g. $C_1$-$C_4$ alkoxy, and preferably di-n-butyl. The fluorosulfonate portion can be $C_1$-$C_9$ alkyl, which can contain from 1 to 2 fluorine atoms per carbon (3 for terminal carbon) and can be perfluorinated. Representative examples are triflate, nonaflate, and the like and preferably triflate. Preparation of these materials, are known in the art as described in Evans, D. A. et al., *J. Am. Chem. Soc.*, 1981, Vol. 103, pp. 2127-2129.

The molar ratio of XIV:organic base:dialkylboron reagent:IV is generally in the range of 1.5:2.0:1.4:1.

The inert solvent used can be a $C_1$-$C_4$ halogenated alkane, e.g. dichloromethane, an aromatic hydrocarbon, e.g. benzene, toluene, xylene, a $C_2$-$C_4$ linear or cyclic ether, e.g. diethylether, tetrahydrofuran (THF), and the like, and preferably dichloromethane.

The temperature of this first part of the aldolization is carried out at $-50°$ C. to $0°$ C.

In the second part of the reaction, the pH of the solution is adjusted with e.g. phosphate buffer, and aqueous 30% hydrogen peroxide is added to oxidize the boron aldolate at a temperature in the range of $-5°$ to $5°$ C.

Conventional workup of the reaction yields V in yields of 80 to 90%. See also: (a) Evans, D. A.; Ennis, M. D.; Mathre, D. J., *J. Am. Chem. Soc.*, 1982, 104, pp. 1737-1739; (b) Evans, D. A.; Bender, S. L.; Morris, J., *J. Am. Chem. Soc.*. 1988, 110, pp. 2506-2526.

Referring to Flow Sheet B, the butanal 4 is reacted with a solution containing p-methoxybenzyloxyacetimide, triethylamine and di-n-butylboron triflate at $-50°$ C. under nitrogen and stirred for about 1½ hours. The pH is adjusted to 7 by the addition of phosphate buffer and 30% aqueous hydrogen peroxide added at 0° C. Conventional workup yields 84% of product 5.

The conversion of V to VI involves removing the oxazolidinone ring system of the aldol adduct V, and replacing it with an amide group. In general, V is added to a stirred mixture of a dialkyl N,O-hydroxylamine and trialkyl aluminum in an inert solvent at 0°-25° C.

The alkyl groups of the dialkyl N,O-hydroxylamine amide independently can be methyl, ethyl, and the like, and preferably methyl, which is commercially available.

The trialkylaluminum reagent functions to form an aluminum amide reagent and can be trimethyl, triethyl, tri-n-butyl aluminum and the like, preferably methyl. These materials are known in the art.

The reaction is conducted in an inert solvent of the same class as described above for the preparation of V including $C_2$-$C_6$ linear or cyclic ethers, including diethyl ether, tetrahydrofuran, halogenated $C_1$-$C_4$ alkanes, including dichloromethane, aromatic hydrocarbons, including toluene, xylene, and the like. Preferred is a mixture of tetrahydrofuran/toluene.

Referring to Flow Sheet B, a specific example is seen where 5 is reacted with trimethylaluminum, N,-O-dimethylhydroxylamine hydrochloride in THF solvent at 0°-25° C. for 1-2 hours to yield 84% of 6 after conventional workup.

The conversion of VI to VII involves reacting the halo ether XIII with lithium metal in an inert solvent at 0° C. followed by addition to VI. The resulting adduct is then treated with an ammonium salt to quench the tetrahedral intermediate and form the ketone VII.

The compound XIII, used in the conversion of VI to VII, can be prepared by conventional methods in the art. Specific synthesis of 13 from 12 and 11, commercially available, is shown in Flow Sheet B. $P_2$ is independently chosen from the same group of conventional hydroxy protecting groups, described above, as P, and $P_1$ with the proviso that $P_2$ is not the same as P.

The inert solvents useful in this condensation step from VI to VII include $C_2$-$C_6$ linear and cyclic ethers including THF, diethylether, dimethoxyethane, and the like, and preferably a mixture of THF/diethylether.

In the first part of the reaction, XIII is reacted with lithium under anhydrous conditions at about 0° C. in a molar ratio of Li:XIII of about 20:1 to form the Li salt.

In the next part of the reaction, a solution containing lithiated XIII is added to VI.

The temperature of the condensation is usually conducted at about $-70°$ to $-60°$ C. for a sufficient period of time, e.g. ½ to 1 hour to effect a sufficient yield.

The resulting adduct is treated in situ with an ammonium salt, e.g. $NH_4Cl$, $NH_4Br$, for a sufficient to react with excess lithium reagent present.

After conventional workup, yields are in the range of 50 to 75%.

For example, referring to Flow Sheet B, compound 13 is treated with lithium in diethyl ether at 0° C. and stirred. The solution of lithiated XIII is then added to amide 6 at $-78°$ C. and stirred. After conventional workup, the yield of 7 is about 69%.

The conversion of VII to VIII involves reduction of the ketone to an alcohol. This involves a reducing agent, e.g. tetramethyl ammonium borohydride acetate in an inert solvent system, e.g. acetonitrile and acetic acid at about a temperature in the range of $-45°$ to 20° C. See also: Evans, D. A.; Carreira, E. M.; Chapman, K. T., *J. Am. Chem. Soc.*, 1988, 110, pp. 3560-3578.

The inert solvents which can be used include acetonitrile, cyclic ethers, e.g. THF, weak organic acids, e.g. acetic acid, and the like, mixtures thereof, and preferably acetonitrile/acetic acid mixture. Preferably the solvent also contains 3 volume percent water.

The temperature is carried out in the range of about $-40°$ to $-10°$ C. and preferably, $-40°$ C., for a sufficient period of time to effect the reduction.

For example, 7 is added to tetramethyl ammonium triacetoxy borohydride in acetonitrile and acetic acid (plus 3 volume percent water) at $-40°$ C. for about 14 hours. Conventional workup results in a 90-95% yield of 8.

The conversion of VIII to IX involves methylation of the hydroxyl group at positions C-13 and C-15 (see Flow Sheet A). This is generally accomplished by adding a methylating agent, e.g. methyl iodide, methyl bromide, and the like, preferably methyl iodide, to a salt of VIII, e.g. sodium salt in an inert solvent, at a temperature of about 0°–25° C., for a sufficient time to effect a significant yield of IX.

Referring to Flow Sheet B, 8 is treated with sodium hydride in THF and then methyl iodide at room temperature to result in a 98% yield of 9.

The conversion of IX to X as illustrated in Flow Sheet A is carried out for the purpose of converting hydroxy protecting group $P_1$ to $P_2$ and exchanging hydroxy protecting group P with $P_3$. The group $P_3$ is a $C_1$–$C_{10}$ alkanoyl hydroxy protecting group and is added for the purpose of producing the precursor to same compound 3, as illustrated in the total synthesis of FK-506 on the T. Jones et al., reference, supra.

The specific synthesis of 9 to 10 is illustrated on Flow Sheet B and described in Example 8.

The hydroxy groups are differentiated in X such that the $C_{10}$ hydroxy can be deprotected first and utilized directly in FK-506 total synthesis (see T. Jones et al., supra). Alternately, the $C_{18}$ hydroxy can be deprotected first to synthesize new FK-506 derivatives.

The following examples are illustrative for purposes of carrying out the instant invention and should not be construed as being limitations on the scope or spirit of the instant invention.

EXAMPLE 1

[2R]-Benzyl 2-methyl-4-penten-1-yl ether 3

A 250-mL round-bottomed flask, equipped with a magnetic stirring bar and a thermometer was fitted with a septum and a nitrogen inlet. The apparatus was charged with 1.60 g (40.0 mmol) of a 60% dispersion of sodium hydride in mineral oil. The sodium hydride was washed with 3×20 mL of dry hexane and then suspended in 40 mL of dry N,N-dimethylformamide and cooled to 0° C. To the stirred suspension was added 4.32 mL (6.21 g, 36.3 mmol) of benzyl bromide followed by dropwise addition of 3.47 g (34.6 mmol) of ketone 2 (via cannula) dissolved in 10 mL of diethyl ether over 15 min maintaining the reaction temperature at 6° C. or less. The reaction mixture was stirred for 20 minutes at 0° C., then warmed to room temperature. After 12 hours, 10 mL of water was cautiously added and the mixture was transferred to a 250-mL separatory funnel. The aqueous Phase was extracted with 3×100 mL of ethyl acetate. The organic layers were individually washed with 100 mL of brine, combined, dried over sodium sulfate, filtered, concentrated and chromatographed (6 cm×33 cm column, 9:1 hexane:dichloromethane) to afford 5.93 g (89%) of benzyl ether 3 as a clear, colorless liquid: $R_f$=0.20 (9:1 hexane:dichloromethane). $[a]_{546}^{22}$ −1.6° (c 2.21, $CH_2Cl_2$). IR(film): 3080m, 3070m, 3035m, 3005w, 2980s, 2960s, 2930s, 2910s, 2880s, 2860s, 2975w, 1645m, 1605w, 1495m, 1480w, 1455s, 1445m, 1415w, 1375m, 1365m, 1310w, 1255w, 1205w, 1160w, 1100s, 1040m, 995m, 915s, 745s, 695s, 605m. 1H-NMR: 7.36–7.24 (m, 5H, ArH); 5.85–5.72 (m, 1H, CH=$CH_2$); 5.06–5.00 (m, 2H, CH=$CH_2$); 4.51 (s, 2H, ArCH$_2$O); 3.33 (dd, J=9.1, 6.2, 1H, one of $CH_2$OBn); 3.28 (dd, J=9.1, 6.2, 1H, one of $CH_2$OBn); 2.27–2.19 (m, 1H, CHCH$_3$); 1.98–1.84 (m, 2H, $CH_2$CH=$CH_2$); 0.93 (d, J=6.5, 3H, CHCH$_3$). $^{13}$C NMR: 138.7, 136.8, 128.2, 127.4, 127.3, 115.8, 75.2, 72.9, 38.0, 33.3, 16.7. Anal. Calcd. for $C_{13}H_{18}O$: C, 82.06; H, 9.53. Found: C, 82.08; H, 9.49.

EXAMPLE 2

[3R]-4-Benzyloxy-3-methylbutanal 4

A 250 mL round-bottomed flask, equipped with a magnetic stirring bar and a thermometer was fitted with a septum and a nitrogen inlet. The apparatus was charged with benzyl 2-methyl-4-penten-1-yl ether (2.39 g, 12.5 mmol) in 75 mL of acetone and 25 mL of water. Osmium tetroxide (0.833 mL of an 0.15 M aqueous solution, 0.125 mmol) was added in one portion, followed by potassium periodate (6.04 g, 26.2 mmol) in three equal portions. The resulting slurry was stirred for 6 hours at room temperature and decanted into a 500 mL separatory funnel. The aqueous layer was extracted with 3×200 mL of diethyl ether. Each washing was stirred over the solids for 5 minutes, washed with 150 mL of saturated aqueous sodium thiosulfate and 100 mL of saturated aqueous sodium chloride. The combined organic layers were dried over sodium sulfate, filtered, concentrated and chromatographed (4×20 cm column; 4:1 hexane:ethyl acetate) to afford 1.94 g (81%) of aldehyde 4 as a colorless oil. $R_f$=0.37 (4:1 hexane:ethyl acetate).

Anal. Calcd. for $C_{12}H_{16}O_2$: C, 74.96; H, 8.29. Found: C, 74.96; H, 8.29.

EXAMPLE 3

Aldol adduct 5

A 100-mL, three-neck, round-bottom flask was fitted with a magnetic stirring bar, nitrogen inlet, thermometer and septum. The apparatus was flushed with nitrogen and then charged with 5.35 g (15.1 mmol) of the p-methoxybenzyloxyoxazolidinone 14, in 30 mL of degassed, sieve-dried dichloromethane and cooled to −50° C. To this clear solution was added 2.31 mL (1.78 g, 16.6 mmol) of triethylamine followed by 3.75 mL (4.13 g, 15.1 mmol) of di-n-butylboron triflate over 5 min. The solution exothermed to −36° C. upon addition of di-n-butylboron triflate. After stirring at −50° C. for 90 min, 1.93 g (10.0 mmol) of aldehyde 4 (previously azeotroped with 2×5 mL of benzene) in 2 mL dichloromethane (plus a 1 mL rinse) was added via cannula. The resulting pale yellow solution was stirred at −40° C. for 1 hours, then warmed to 0° C. over 10 minutes. The reaction was quenched by addition of 15 mL of pH 7 phosphate buffer followed by 10 mL of methanol and 10 mL of tetrahydrofuran to result in a nearly homogeneous solution. After 5 min, 15 mL of 30% aqueous hydrogen peroxide in 15 mL methanol was added dropwise over 30 min (caution: initial reaction is highly exothermic). After stirring for 1 hour at 0° C. the reaction mixture was concentrated by rotary evaporation. The resulting mixture was extracted with 3×100 mL of ethyl acetate. The individual organic extracts were washed with 100 mL of saturated aqueous sodium bicarbonate and 100 mL of brine. The organic layers were combined, dried over sodium sulfate, filtered and concentrated. The resulting oil was chromatographed (6.5 cm×35 cm column, 2:1 hexane:ethyl acetate) to provide 4.62 g (84%) product. $[a]_D^{28}$+31.8° (c 2.08, $CH_2Cl_2$). $R_f$=0.16 (2:1 hexane:ethyl acetate).

Anal. Calcd. for $C_{32}H_{37}NO_7$: C, 70.18; H, 6.81; N, 2.56. Found: C, 70.00; H, 6.98; N, 2.70.

EXAMPLE 4

Amide 6

To a suspension of 3.46 g (35.5 mmol) of N,O-dimethyl-hydroxylamine hydrochloride in 18 mL of tetrahydrofuran at 0° C. in a 250 mL round-bottom flask fitted with a magnetic stirring bar, septum, thermometer and nitrogen inlet was added 17.8 mL (35.5 mmol) of 2.0 M trimethylaluminum in toluene over a 5 minute period (caution: vigorous gas evolution). After the addition was complete, the cooling bath was removed and the clear solution was stirred for 30 minutes at room temperature. The solution was recooled to $-15°$ C., and a solution of 3.89 g (7.1 mmol) of imide 5 in 18 mL of tetrahydrofuran (plus a 5 mL rinse) was added via cannula. The cloudy reaction mixture was stirred at $-10°$ C., at which temperature gas evolved steadily and the mixture slowly cleared. After 2 hours the solution was cannulated into a mixture of 150 mL of hexane, 20 mL of dichloromethane and 100 mL of 1.0 N aqueous tartaric acid at 0° C. The resulting two phase mixture was stirred at 0° C. for 1 hour. The layers were separated and the aqueous layer was extracted with $2 \times 150$ mL of dichloromethane. The individual organic extracts were washed with $2 \times 100$ mL of brine, combined, dried over sodium sulfate, filtered, and concentrated. Purification of the residue by chromatography (6 cm$\times$30 cm column, a gradient consisting of: 2 L of 5:1 dichloromethane:ethyl acetate, followed by 1 L of 4:1, 1 L of 3:2, and 1 L of 1:1) gave 2.58 g (84%) of 6 $[a]_D^{27}+31.5°$ (c 3.60, $CH_2Cl_2$). $R_f=0.19$ (1:1 hexane:ethyl acetate).

Anal. Calcd. for $C_{24}H_{33}NO_6$: C, 66.80; H, 7.71; N, 3.25. Found: C, 66.65; H, 7.82; N, 3.24.

EXAMPLE 5

Ketone 7

A 50 mL pear-shaped flask was fitted with a septum, thermocouple, nitrogen inlet and magnetic stirring bar, flushed with nitrogen, and charged with 1.09 g (39.4 mmol) of high sodium (0.5%) 25 wt% lithium dispersion in mineral oil. The dispersion was washed with $4 \times 3$ mL of distilled diethyl ether (lithium floats in diethyl ether and coats the walls of the flask when solvent is removed beneath it) and then suspended in 5 mL of distilled diethyl ether. A crystal of iodine was added and the suspension was cooled to 0° C. To the gray suspension was added via cannula 3.16 g (11.8 mmol) of bromide 13 dissolved in 8 mL (plus $2 \times 2$ mL rinse) of distilled diethyl ether. The suspension was stirred 1 hour at 0° C. (within 15 minutes the suspension turned rust red). A separate 50 mL round-bottom flask was fitted with a septum, thermocouple, nitrogen inlet and magnetic stirring bar, flushed with nitrogen, and charged with 0.850 g (1.97 mmol) of amide 6 dissolved in 5 mL of distilled tetrahydrofuran. Both reaction vessels were cooled to $-78°$ C. and the organolithium reagent was transferred to the amide solution via cannula. An exotherm to $-50°$ C. was observed. After stirring at $-78°$ C. for 30 minutes, the reaction mixture was warmed to $-20°$ C., stirred 30 minutes, and then transferred via cannula to a well-stirred mixture of 50 mL of saturated aqueous ammonium chloride and 20 mL of diethyl ether at 0° C. The resulting mixture was transferred to a separatory funnel and extracted with $3 \times 20$ mL of ethyl acetate. The organic layers were combined, dried over sodium sulfate, filtered, concentrated and chromatographed (4.5 cm$\times$30 cm column, 7:1 hexane:ethyl acetate) to provide 759 mg (69%) of ketone 7 as a clear oil. $[a]_D^{28}+29.2°$ (c 1.08, $CH_2Cl_2$). $R_f=0.28$ (4:1 hexane:ethyl acetate).

Anal. Calcd. for $C_{32}H_{50}O_6Si$: C, 68.78; H, 9.02. Found: C, 68.63; H, 9.19.

EXAMPLE 6

Diol 8

A 15 mL round-bottom flask fitted with a septum, nitrogen inlet and magnetic stirring bar was charged with 195 mg (0.741 mmol) of tetramethylammonium triacetoxyborohydride, 0.5 mL of acetonitrile and 0.25 mL of acetic acid. The mixture was stirred at room temperature for 10 minutes and then cooled to $-40°$ C. A solution of 0.103 g (0.185 mmol) of ketone 7 in 0.5 mL of acetonitrile and 0.100 mL of water was added to the reaction mixture via cannula. After stirring at $-40°$ C. for 14 hours, 1 mL of acetone was added and the reaction was warmed to 0° C. and stirred for 20 minutes. The ice bath was removed and 2 mL of a 1 M solution of sodium potassium tartrate was added. The resulting slurry was stirred at room temperature for 30 minutes. The mixture was neutralized by the cautious addition of saturated aqueous sodium bicarbonate. The resulting clear solution was extracted with $4 \times 20$ mL of ethyl acetate. The organic layers were combined, dried over sodium sulfate, filtered, concentrated and chromatographed (2 cm$\times$20 cm column, 3:1 hexane: ethyl acetate) to afford 87 mg (84%) of inseparable diols 8 (isomer at $C_{13}$) as an oil that solidified on standing. HPLC analysis of the crude reaction mixture (220 nm UV detection; Zorbax RX reverse phase column, a gradient from 70:30 acetonitrile:water to 100% acetonitrile at 15 minutes) showed a 91.5:8.5 ($R_t=13.8$ min, minor; 14.3 min, major) mixture of isomers. $R_f=0.22$ (4:1 hexane:ethyl acetate).

Anal. Calcd. for $C_{32}H_{52}O_6Si$: C, 68.53; H, 9.35. Found: C, 68.82; H, 9.66.

EXAMPLE 7

Dimethyl ether 9

A 15 mL round-bottom flask fitted with a septum, nitrogen inlet and magnetic stirring bar was charged with 50 mg (1.25 mmol) of 60% sodium hydride dispersion and 1 mL of distilled tetrahydrofuran. To the suspension was added 156 mL (355 mg, 2.50 mmol) of methyl iodide and 140 mg (0.250 mmol) of diol 8 at room temperature. The reaction was stirred at room temperature for 2 hours and cautiously quenched by the addition of 5 mL of saturated aqueous ammonium chloride. The reaction mixture was extracted with $3 \times 10$ mL of ethyl acetate. The organic layers were combined, dried over sodium sulfate, filtered, concentrated and chromatographed (2 cm$\times$20 cm column, 8:1 hexane:ethyl acetate) to provide 137 mg (93%) of dimethyl ether 9.

EXAMPLE 8

Bis-TBS-ether 10

A 25 mL round-bottomed pressure flask was charged with 927 mg (1.57 mmol) of benzyl ether 9, 0.120 g of 20% Pd(OH)$_2$ on carbon and 10 mL of ethyl acetate. The flask was placed under 34 psi of hydrogen and rocked for 36 hours. The resulting slurry was filtered through Celite ®, concentrated and chromatographed (4 cm$\times$25 cm column, 1:1 hexane:ethyl acetate) to provide 509 mg (85%) of the corresponding diol. The diol (509 mg, 1.34 mmol) was dissolved in 5 mL of dry pyridine and cooled to 0° C. under nitrogen. Pivaloyl chloride (168 mg, 171 mL, 1.39 mmol) was added and the reaction was stirred at 0° C. for 4 hours. The reaction was quenched by the addition of 10 mL of water. The resulting mixture was extracted with 4×20 mL of ethyl acetate. The organic extracts were combined, dried over sodium sulfate, filtered, concentrated and chromatographed (3 cm×20 cm column, 4:1 hexane:ethyl acetate) to provide 565 mg (91%) of the primary ester. A 25 mL round bottom flask fitted with a magnetic stirring bar, nitrogen inlet and thermocouple was charged with 520 mg (1.12 mmol) of the primary ester, 2 mL of dichloromethane, and 262 μL (240 mg, 2.25 mmol) of 2,6-lutidine. The mixture was cooled to 0° C. and 310 μL (356 mg, 1.35 mmol) of t-butyldimethylsilyl trifluoromethane sulfonate was added. The resulting clear solution was stirred 30 minutes at 0° C. and quenched by the addition of 10 mL of saturated aqueous sodium bicarbonate. The mixture was extracted with 3×15 mL of ethyl acetate. The organic layers were combined, dried over sodium sulfate, filtered, concentrated and chromatographed (3 cm×20 cm column, 9:1 hexane:ethyl acetate) to provide 640 mg (99%) of 10.

EXAMPLE 9

[2S]-3-t-butyldimethylsilyloxy-2-methylpropanol (12)

A 250 mL round-bottom flask fitted with a magnetic stirring bar, septum and nitrogen inlet was charged with 100 mL of N,N-dimethylformamide, 6.08 g (51.5 mmol) of (s) methyl 3-hydroxy-2-methylpropionate, 6.31 g (92.6 mmol) imidazole and 10.9 g (72.1 mmol) of t-butyldimethylsilyl chloride. The reaction exothermed to +30° C. and was allowed to stir at room temperature. After 5 hours, 100 mL of saturated aqueous sodium bicarbonate was added and the reaction mixture was extracted with 3×150 mL of hexane. The organic layers were washed with 2×100 mL of water, combined, dried over sodium sulfate, filtered, and concentrated to provide 14.1 g (118%) of the silylated ester. The crude product was suitable for reduction. A 500 mL round-bottom flask fitted with a magnetic stirring bar, septum and nitrogen inlet was charged with 79 mL (118 mmol) of a 1.5 M solution of diisobutylaluminum hydride in toluene and 80 mL of tetrahydrofuran. The reaction mixture was cooled to −70° C. and 11 g (47.3 mmol) of the crude silylated ester was dissolved in 40 mL of tetrahydrofuran and added via cannula. The reaction mixture was stirred 20 minutes at −60° C. and then rapidly warmed to 0° C. and stirred for 2 hours. The reaction was then transferred via cannula into a well-stirred mixture of 300 g of sodium potassium tartrate in 1000 mL of water and 300 mL of hexanes. The resulting slurry was stirred until two clear layers separated (approximately 2 hours). The layers were separated and the aqueous layer was extracted with 3×200 mL of diethyl ether. The organic layers were combined, dried over sodium sulfate, filtered, concentrated and chromatographed (6 cm × 30 cm column, dichloromethane) to provide 6.19 g (80% for two steps) of alcohol 12. $[a]_D^{31} + 9.44°$ (c 1.97, $CH_2Cl_2$). $R_f = 0.23$ (dichloromethane).

Anal. Calcd. for $C_{10}H_{24}O_2Si$: C, 58.77; H, 11.84. Found: C, 58.49; H, 12.02.

EXAMPLE 10

[2S]-3-t-butyldimethylsilyloxy-2-methylpropyl bromide (13)

A 250 mL round-bottom flask fitted with a magnetic stirring bar, septum and nitrogen inlet was charged with 6.19 g (30.3 mmol) of alcohol 12 and 50 mL of dichloromethane. The solution was cooled to −10° C. and 8.60 mL (6.24 g, 61.6 mmol) of triethyl amine was added followed by addition of 3.45 mL (5.10 g, 44.5 mmol) of methanesulfonyl chloride over 15 minutes. The resulting mixture was stirred at −10° C. for 1 hour and then quenched by the addition of 50 mL of 0.5 N sodium bisulfate. The reaction mixture was extracted with 4×50 mL of dichloromethane. The organic layers were combined, dried over sodium sulfate, filtered, concentrated and rapidly chromatographed (6 cm×25 cm column, 1:1 hexane:ethyl acetate) to provide 8.48 g (99%) of the mesylate. The mesylate was immediately converted to the bromide. A 100 mL round-bottom flask fitted with a magnetic stirring bar, condenser and nitrogen inlet was charged with 8.48 g (30.0 mmol) of the mesylate, 50 mL of acetone and 29.0 g (90.0 mmol) of tetrabutylammonium bromide. The solution was heated to reflux for 6 hours and cooled to room temperature. A two phase mixture was formed by the addition of 100 mL of diethyl ether and 150 mL of water. The aqueous layer was extracted with 3×100 mL of diethyl ether. The organic layers were combined, dried over sodium sulfate, filtered concentrated, chromatographed (4 cm×25 cm column, hexane) and distilled (b.p. 50° C./0.4 Torr) to give 5.3 g (66%) of bromide 13. $[a]_D^{27} + 11.1°$ (c 1.42, $CH_2Cl_2$). $R_f = 0.80$ (1:1 hexane:dichloromethane).

Anal. Calcd. for $C_{10}H_{23}OSiBr$: C, 44.94; H, 8.67. Found: C, 44.54; H, 8.98.

What is claimed is:

1. A process comprising the steps of:
   (a) contacting III with an oxidizing agent in an inert solvent and of a temperature in the range of 0 to 50° C. for a

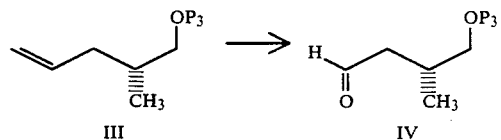

sufficient time to form the oxidation product IV, where $P_3$ is a hydroxy protecting group;

(b) contacting IV with a solution of a chiral N-acyloxazolidinone XIV, where Y is Protected oxymethyl, which is stable under the reaction conditions, and trialkylamine, and dialkylboron trifluoroalkylsulfonate under an inert atmosphere in an inert solvent and at a temperature in the range of −100° to 25° C. for a sufficient time to form the aldol addition product V, wherein $R_1$ and $R_2$ are independently chosen from H, $C_1$–$C_4$ linear or branched alkyl, benzyl, phenyl, which may be substituted with halo or $C_1$–$C_4$ alkoxy, with the proviso that $R_2$ is not H,

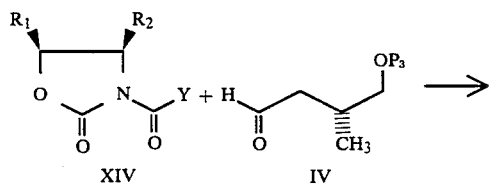

and where P₁ is a hydroxy protecting group which may be the same or different than P₃;

(c) contacting V with a solution of trialkylaluminum and N,O-dimethylhydroxylamine hydrochloride in an inert solvent and at a temperature in the range of −30° to 20° C. for a sufficient time to form the amide VI;

(d) contacting VI with XIII in the presence of lithium in an inert solvent therefor at a temperature in the range of −100° to 25° C., followed by contacting the resulting mixture with aqueous ammonium halide at a temperature in the range of −20° to 25° C. for a sufficient time to form the condensation product VII where P₂ is a hydroxy protecting group, which may be the same as P₁ but is different from P₃;

(e) contacting VII with tetraalkylammonium triacetoxy borohydride and a weak organic acid in an inert solvent and at a temperature of about −40° to 25° C., for a sufficient time to form the reduction product VIII;

(f) Contacting VIII with an alkali metal hydride and a methylating agent under anhydrous conditions in an inert atmosphere in an inert solvent and at a temperature in the range of 0° to 50° C. for a sufficient time to form the methylated product IX;

2. A process comprising the step of contacting IV with a solution of a chiral N-acyloxazolidinone XIV, where Y is protected oxymethyl, which is stable under the reaction conditions, and trialkylamine, and a dialkylboron fluoroalkylsulfonate under an inert atmosphere in an inert solvent and at a temperature in the range of −100° to 25° C. for a sufficient time to form the aldol addition product V, wherein R₁ and R₂ are independently chosen from H, C₁-C₄ linear or branched alkyl, benzyl, phenyl, which may be substituted with halo or C₁-C₄ alkoxy with the proviso that R₂ is not H;

and where P₁ is a hydroxy protecting group which may be the same or different than P 3. A process comprising the step of contacting VI with XIII in the presence of lithium in an inert solvent therefor at a temperature in the range of −100° to 25° C., followed

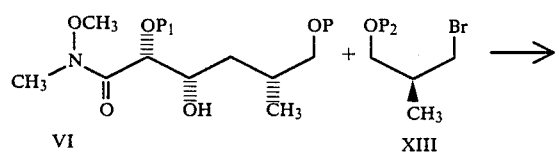

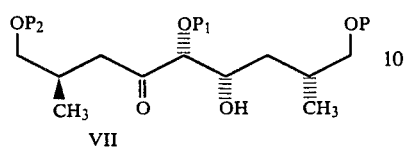

by contacting the resulting mixture with aqueous ammonium halide at a temperature in the range of $-20°$ to $25°$ C. for a sufficient time to form the condensation product VII where $P_2$ is a hydroxy protecting group, which may be the same as $P_1$ but is different from P.

4. A process comprising the steps of:
   (a) contacting 3 with osmium tetraoxide, and $KIO_4$ in acetone/water solvent at about $20°$-$25°$ C. for a sufficient time to form 4:

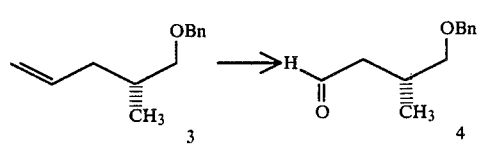

(b) contacting 4 with a solution of 14, triethylamine, di-n-butylboron triflate in methylene chloride solvent at about $-40°$-to-$50°$ C., under nitrogen atmosphere,

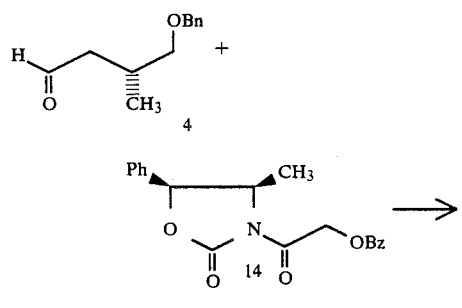

for a sufficient time to form 5;

(c) contacting 5 with a solution of trimethylaluminum, N,O-dimethyl-hydroxylamine hydrochloride in THF at $0°$-$25°$ C. for a sufficient time to form 6;

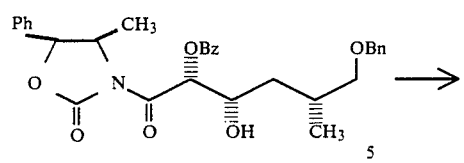

(f) contacting 6 with compound 13 and lithium in dimethylether at $-78°$ C., followed by contacting with aqueous ammonium chloride at $0°$ C. for a sufficient time to form 7;

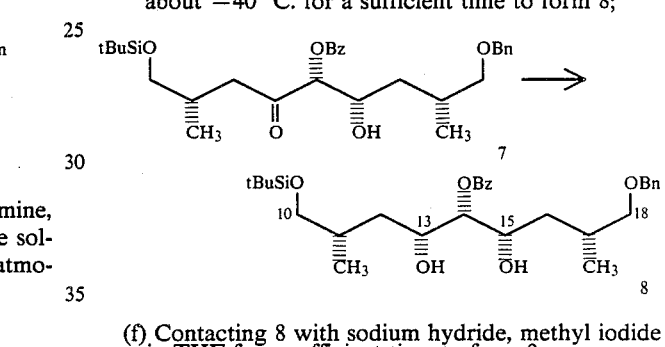

(e) contacting 7 with tetramethylammonium triacetoxy borohydride, acetonitrile and acetic acid at about $-40°$ C. for a sufficient time to form 8;

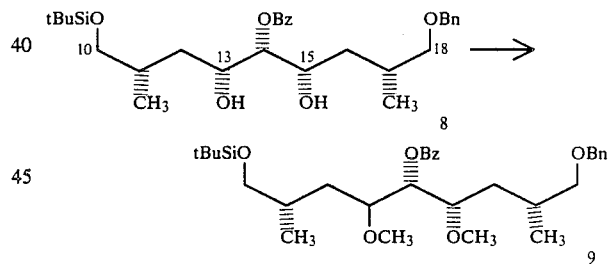

(f) Contacting 8 with sodium hydride, methyl iodide in THF for a sufficient time to form 9:

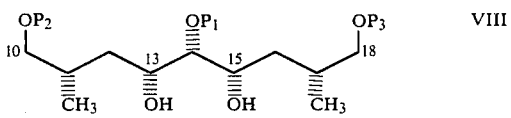

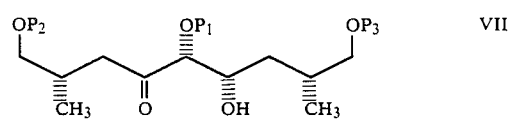

5. A process for the formation of a compound VIII $$\text{VIII}$$

wherein $P_1$, $P_2$ $P_3$ are each independently selected hydroxy-protecting groups; which comprises contacting compound VII $$\text{VII}$$

with tetraalkylammonium tri-acetoxy borohydride and a weak organic acid in an inert solvent containing 3 volume per cent water at a temperature of about $-40°$ to $+25°$ C.

* * * * *